(12) United States Patent
Kim et al.

(10) Patent No.: US 11,585,793 B2
(45) Date of Patent: Feb. 21, 2023

(54) RECOGNITION KITS AND METHODS FOR HARMFUL HEAVY METALS

(71) Applicant: Korea Institute of Ocean Science & Technology, Busan (KR)

(72) Inventors: Kyoungrean Kim, Busan (KR); Aleum Lee, Busan (KR)

(73) Assignee: Korea Institute of Ocean Science & Technology, Busan (KR)

( * ) Notice: Subject to any disclaimer, the term of this patent is extended or adjusted under 35 U.S.C. 154(b) by 253 days.

(21) Appl. No.: 16/891,409

(22) Filed: Jun. 3, 2020

(65) Prior Publication Data
US 2020/0400628 A1    Dec. 24, 2020

(30) Foreign Application Priority Data

Jun. 20, 2019  (KR) .......................... 10-2019-0073575

(51) Int. Cl.
| | |
|---|---|
| *G01N 31/22* | (2006.01) |
| *G01N 21/78* | (2006.01) |
| *G01N 21/25* | (2006.01) |
| *G01N 33/92* | (2006.01) |

(52) U.S. Cl.
CPC .......... *G01N 31/22* (2013.01); *G01N 21/255* (2013.01); *G01N 21/78* (2013.01); *G01N 33/92* (2013.01); *G01N 2405/00* (2013.01)

(58) Field of Classification Search
CPC ...... G01N 31/22; G01N 21/255; G01N 21/78; G01N 33/92
See application file for complete search history.

(56) References Cited

U.S. PATENT DOCUMENTS

2017/0010249 A1*   1/2017  Kim ....................... G01N 33/84

FOREIGN PATENT DOCUMENTS

KR    10-2017-0007902 A    1/2017

OTHER PUBLICATIONS

Application of biosurfactants for heavy metals leaching from immobilized activated sludge Malgorzata Kuczajowska-Zadrozna, Urszula Filipkowska, Tomasz Jozwiak Archives of Environmental Protection vol. 41 No. 1 pp. 43-52 (Year: 2015).*

* cited by examiner

*Primary Examiner* — Brian R Gordon
*Assistant Examiner* — Dwan A Gerido (57) ABSTRACT

The present disclosure relates to a kit and method for testing harmful heavy metals onsite, which can determine the presence or absence of harmful heavy metals and the degree of contamination with harmful heavy metals dissolved in water or contained in sediment, soil, deep-sea mining tailings and the like. The kit includes a receiving member and a diagnostic solution containing a biosurfactant, which is accommodated in the receiving member and undergoes an ion exchange reaction with a liquid including harmful heavy metals or a solid sample from which harmful heavy metals are leached in a liquid phase.

13 Claims, 8 Drawing Sheets

RECOGNITION KITS AND METHODS FOR HARMFUL HEAVY METALS

CROSS REFERENCE TO RELATED APPLICATION

The present application claims priority under 35 U.S.C. § 119(a) to Korean Patent Application No. 10-2019-0073575, filed in the Korean Intellectual Property Office on Jun. 20, 2019, the entire content of which is incorporated herein for all purposes by this reference.

BACKGROUND

1. Technical Field

The present disclosure relates to a kit and method for recognizing harmful heavy metals, which make it easy to determine the presence or absence of harmful heavy metals dissolved in water or contained in sediment, soil, deep-sea mining tailings, and the like.

2. Description of the Related Art

It is very important to determine the presence or absence of harmful heavy metals (qualitative evaluation) and the degree of contamination therewith (quantitative evaluation) in environmental media such as water, soil, sediment and the like.

Typically, in order to evaluate harmful heavy metal content, sampling, storage, pretreatment and analysis methods that differ for each environmental medium are carried out, and a person with expertise and analytical skills has to perform analysis using specific facilities and equipment, and simultaneously, based on the results of analysis of standard reference materials (SRM), a recovery ratio is verified and an analysis value is corrected and used.

This process, particularly the process from sampling onsite to obtain final results through sample transport, storage, pretreatment, analysis and result evaluation, takes at least 5 to 7 days and requires considerable manpower and costs.

Meanwhile, the environmental field has very diverse region-specific characteristics, and differs greatly from the laboratory with regard to surrounding conditions and infrastructure. In particular, if it is possible to quickly determine the presence or absence of harmful heavy metals (qualitative evaluation) and the degree of contamination therewith (quantitative evaluation) in media such as aquatic ecosystem (land, sea) sediment, soil, etc., or at the site of generation of solids such as deep-sea mining tailings, etc., any action required for environmental remediation may be taken immediately.

However, existing methods for analyzing and evaluating harmful heavy metals take a long time, and have a problem in that considerable difficulty is involved in determining and taking remediation measures after determining the presence or absence of the heavy metal in the environmental medium collected at the actual site or the degree of contamination therewith.

SUMMARY

Accordingly, an objective of the present disclosure is to provide a kit and method for testing for harmful heavy metals onsite, which may immediately determine the presence or absence of harmful heavy metals and the degree of contamination with harmful heavy metals dissolved in water or contained in sediment, soil, deep-sea mining tailings and the like, onsite without restrictions as to place or conditions.

In order to accomplish the above objective, the present disclosure provides a kit for recognizing a harmful heavy metal (hereinafter, referred to as a "kit of the present disclosure") including a receiving member and a diagnostic solution containing at least one biosurfactant, which is accommodated in the receiving member and the color of which changes upon reaction with the harmful heavy metal.

In an exemplary embodiment, the biosurfactant may react with the heavy metal to form a complex, whereby the color of the diagnostic solution may change, and the amount of the complex is in proportion to the amount of the heavy metal.

In an exemplary embodiment, the biosurfactant may be sodium alginate.

In an exemplary embodiment, the biosurfactant may be a mixture of sodium alginate and rhamnolipid.

In an exemplary embodiment, the kit of the present disclosure may further include a display part including a light irradiation module radiating light to one side of the receiving member, a light acquisition module obtaining light transmitted to the opposite side of the receiving member, an analysis module comparing the amount of light radiated by the light irradiation module with the amount of light obtained by the light acquisition module to obtain a result value, and a display module displaying the result value of the analysis module.

In addition, the present disclosure provides a method of recognizing a harmful heavy metal (hereinafter, referred to as a "method of the present disclosure") including manufacturing the above kit for recognizing a harmful heavy metal (S10), placing a sample in the receiving member of the kit to allow the sample to react with a diagnostic solution (S20), and recognizing the presence or absence of the harmful heavy metal in the sample by visually observing a color change in the diagnostic solution (S30).

In an exemplary embodiment, the method of the present disclosure may further include recognizing the presence or absence of the harmful heavy metal in the sample based on data on radiated light using the display part (S40).

In S40, a predetermined amount of light is radiated to one side of the receiving member, light transmitted to the opposite side of the receiving member is obtained, and the amount of light thus obtained is analyzed with a comparison value to thus display the presence or absence of the heavy metal in the sample.

According to the present disclosure, a kit and method for recognizing harmful heavy metals can immediately determine the presence or absence of harmful heavy metals and the degree of contamination with harmful heavy metals dissolved in water or contained in sediment, soil, deep-sea mining tailings and the like, onsite without restrictions as to place or conditions, thus minimizing the time, manpower and costs required for evaluation and enabling subsequent measures to be quickly performed onsite depending on the degree of contamination.

DESCRIPTION OF SPECIFIC EMBODIMENTS

Hereinafter, a detailed description will be given of constructions and functions of the present disclosure with reference to the accompanying drawings. The terms or words used in the description and the claims of the present disclosure should be interpreted as having meanings and concepts of the disclosure in keeping with the spirit of the invention based on the principle that the inventors can appropriately define the terms in order to describe the invention in the best way.

The kit of the present disclosure includes a receiving member and a diagnostic solution containing at least one biosurfactant, which is accommodated in the receiving member and the color of which changes upon reaction with a harmful heavy metal.

Specifically, in the kit of the present disclosure, a sample collected onsite is placed in the receiving member containing the diagnostic solution and allowed to react with the diagnostic solution, and when there is a change in the color of the diagnostic solution, the presence or absence of the harmful heavy metal in the sample may be visually observed.

Here, the mechanism of color change is one whereby the color of the diagnostic solution is changed to a visible extent by forming a complex by reacting the biosurfactant in the diagnostic solution with a heavy metal, as described below.

The receiving member serves to accommodate the biosurfactant therein, and may include any one appropriately selected from among a variety of known receiving members having internal spaces. For example, the receiving member may be a test tube.

The diagnostic solution is accommodated in the receiving member, which is a reagent that reacts with a heavy metal contained in an environmental medium to be evaluated, for example, water, sediment, soil, deep-sea mining tailings, etc., which is placed in the receiving member, and the diagnostic solution undergoes an ion exchange reaction with a heavy metal to form a complex.

Here, the environmental medium may be in the form of a liquid containing a harmful heavy metal or in the form of a solid from which a harmful heavy metal is leached in a liquid phase.

Here, the biosurfactant includes sodium alginate.

Sodium alginate is a polysaccharide that may be mainly collected from brown algae such as kelp, etc., and is composed of α-L-guluronic acid and (1-4)-linked β-D-mannuronic acid.

Sodium alginate has properties such as biocompatibility, non-toxicity, biodegradability, hydrophilicity and the like, is known to exhibit viscosity when dissolved in an aqueous solution, and is mainly used in industries such as food, pharmaceuticals, etc.

Sodium alginate is represented by Chemical Formula 2 below.

[Chemical Formula 2]

$(C_6H_8O_6)_n$

In particular, the biosurfactant may further include rhamnolipid, in addition to sodium alginate.

Rhamnolipid is a glycolipid produced by microorganisms in the genus *Pseudomonas*, and acts to increase the water solubility of an organic compound by lowering the surface tension of a liquid, like other surfactants.

Also, rhamnolipid has high biodegradability and low toxicity, and is utilized in various industrial fields such as those of oil recovery, agriculture, washing, cosmetics, and pharmaceuticals due to these properties.

The rhamnolipid molecule is composed of a rhamnose sugar molecule including β-hydroxy fatty acid, and is represented by Chemical Formula 1 below.

[Chemical Formula 1]

Representative monorhamnolipid: Rha—$C_{10}$—$C_{10}$ (n=6)

Representative dirhamnolipid: Rha—Rha—$C_{10}$—$C_{10}$ (n=6)

Figure 1:
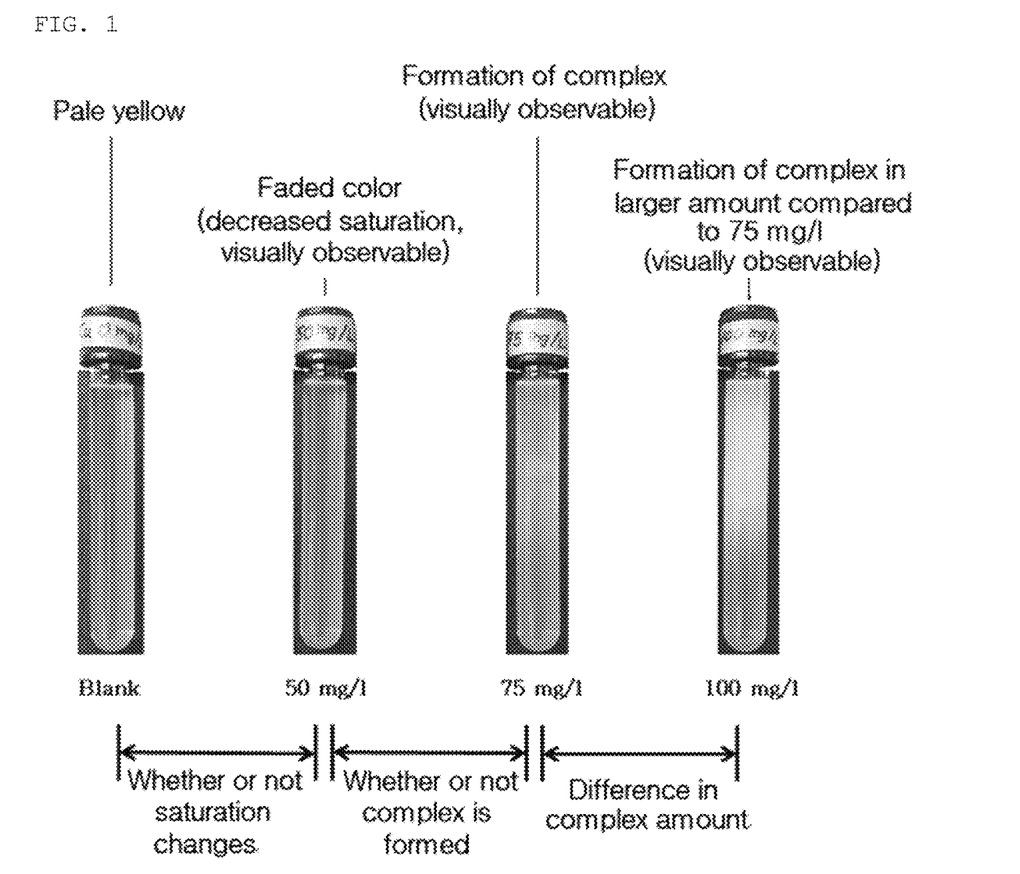
FIG. 1 shows determination of the presence or absence of harmful heavy metals and the degree of contamination therewith.
Figure 2:
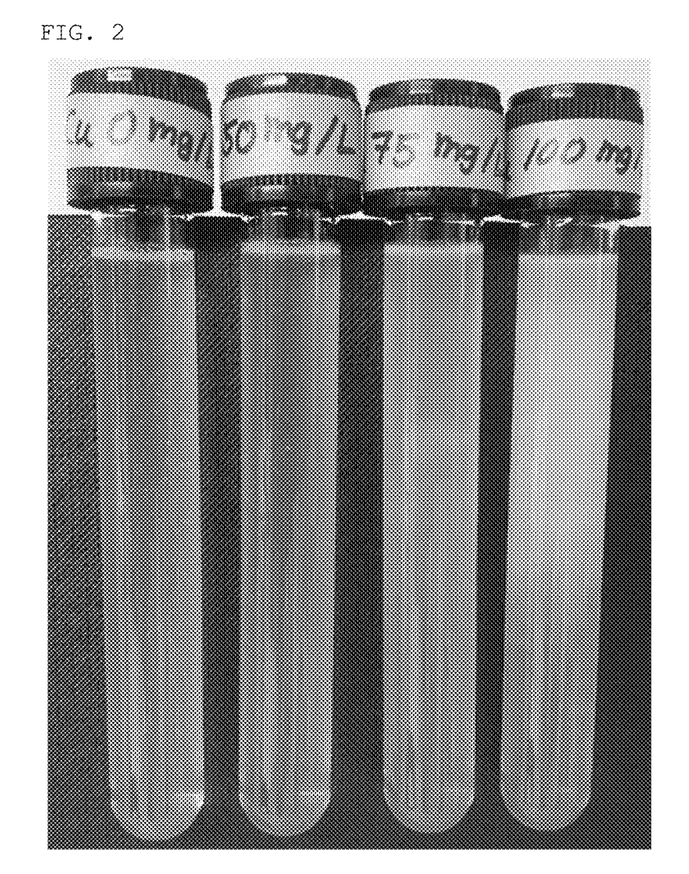
FIG. 2 shows a change in the color of a kit of the present disclosure depending on the concentration of copper (Cu) in a diagnostic solution.
Figure 3:
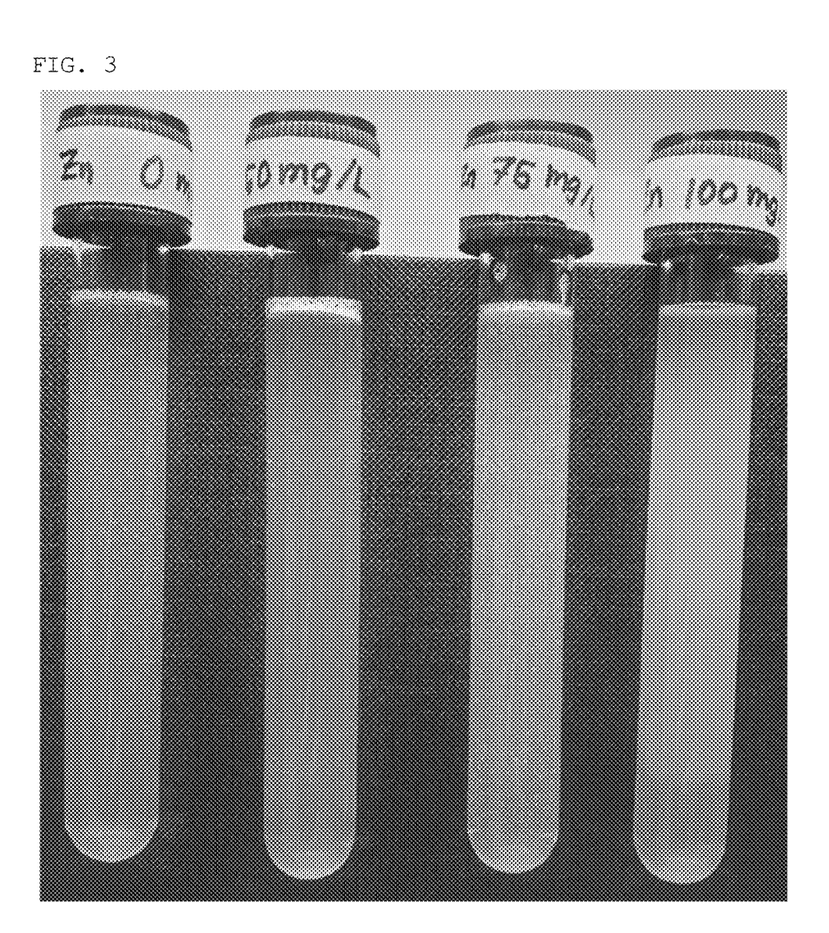
FIG. 3 shows a change in the color of the kit of the present disclosure depending on the concentration of zinc (Zn) in a diagnostic solution.
Figure 4:
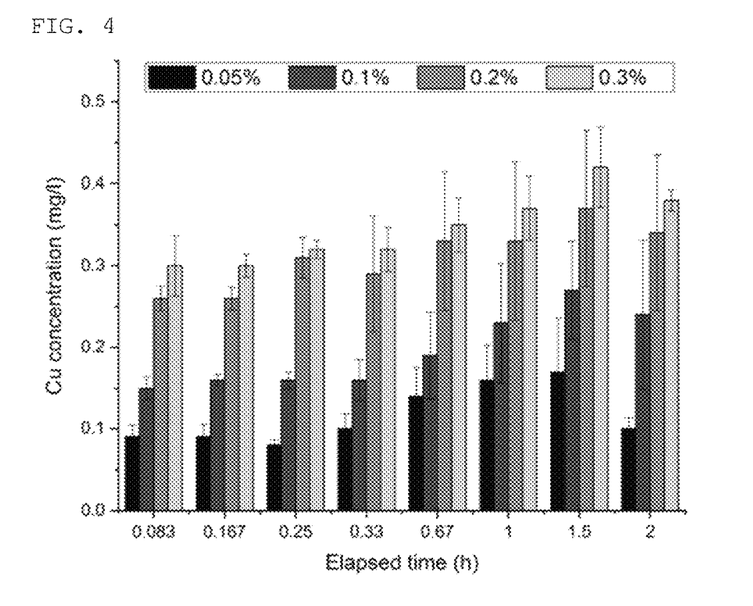
FIGS. 4 and 5 are graphs showing leaching of copper (Cu) depending on the elapsed time and the amount of an additive including a biosurfactant.
Figure 5:
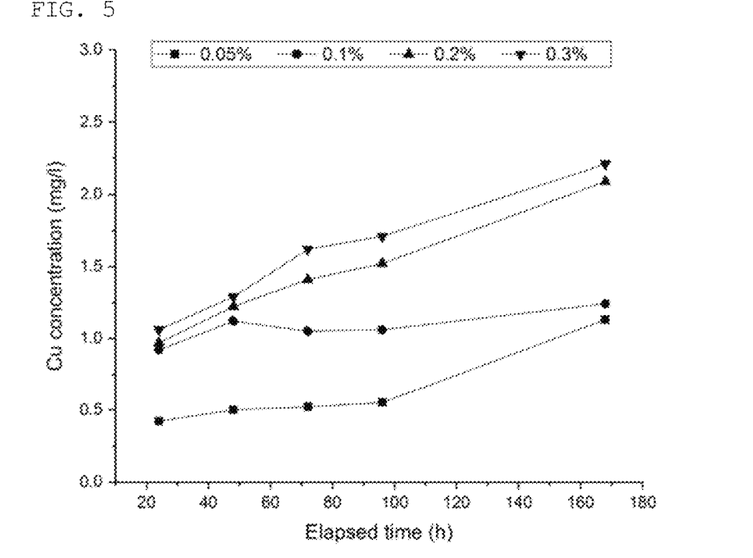

When the biosurfactant such as rhamnolipid and sodium alginate is used as an additive in the technical field of remediation of sediment, soil and deep-sea mining tailings, as shown in FIGS. 4 and 5, it is known that the amount of the harmful heavy metal that is leached, including copper (Cu), etc., in chemical treatment is affected by the amount of additive and the elapsed time.

FIG. 4 is a graph showing the effect of the amount of the biosurfactant that is added on the leaching of copper (Cu) from a manganese nodule sample (particle size range: 63-20 μm, 2% Sol.) for a short reaction time (within 2 hr), and FIG. 5 is a graph showing the effect of the amount of the biosurfactant that is added on the leaching of copper (Cu) from a manganese nodule sample (particle size range: 63-20 μm, 2% Sol.) for a long reaction time (within 180 hr).

In the kit of the present disclosure, rhamnolipid and sodium alginate react with a harmful heavy metal to form a visually recognizable complex, which may be utilized to easily recognize the presence or absence of the harmful heavy metal in the sample.

Specifically, when rhamnolipid and sodium alginate are prepared in individually appropriate concentrations and mixed to afford a diagnostic solution, the diagnostic solution may exist in a stable state, making it possible to obtain an effective result in the recognition of the presence or absence of harmful heavy metals from environmental media including water, sediment, soil, deep-sea mining tailings, and the like.

In general, when harmful heavy metals are contained in the liquid, or when harmful heavy metals are leached in a liquid phase from the solid sample, all harmful heavy metals are present in the form of cations in the liquid.

Harmful heavy metals in the form of cations in the liquid are contained in the mixture structure through a chemical ion exchange reaction in a short period of time of approximately several minutes with the diagnostic solution including a mixture of rhamnolipid and sodium alginate, thus forming a stable structure (complex).

As described above, the kit of the present disclosure uses an ion exchange reaction of a cationic material and thus may be applied to all water in the natural environment, for example, sea water, fresh water, and mixed water, because the presence or absence of chlorine ions does not affect the reaction.

This reaction mechanism is described with reference to photographs showing experimental conditions.

Figure 6:
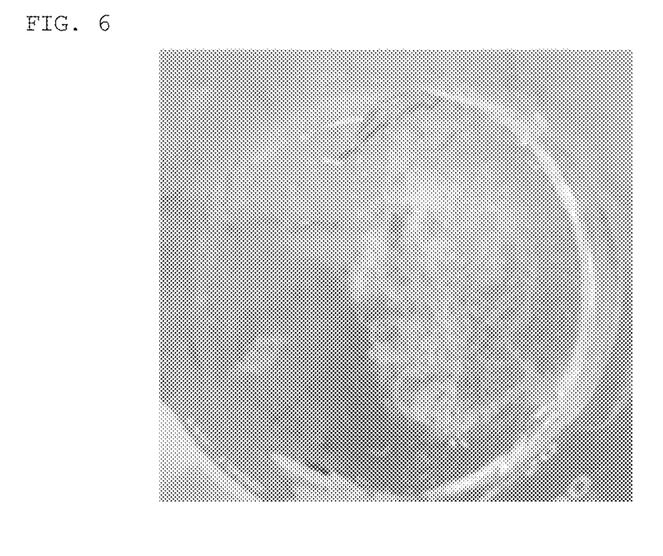
FIG. 6 is a photograph showing the shape of a complex formed by reaction of rhamnolipid and sodium alginate.

As shown in FIG. 6, in the mixture of rhamnolipid and sodium alginate, two materials each having a chain structure have a similar structure and are easily mixed to form a longer chain structure (in the shape of a thread in the photograph). In this way, the mixture of rhamnolipid and sodium alginate forms a longer chain structure, thereby reacting with a heavy metal to form a larger complex than when using sodium alginate alone, ultimately further increasing the visual recognition efficiency.

Figure 7:
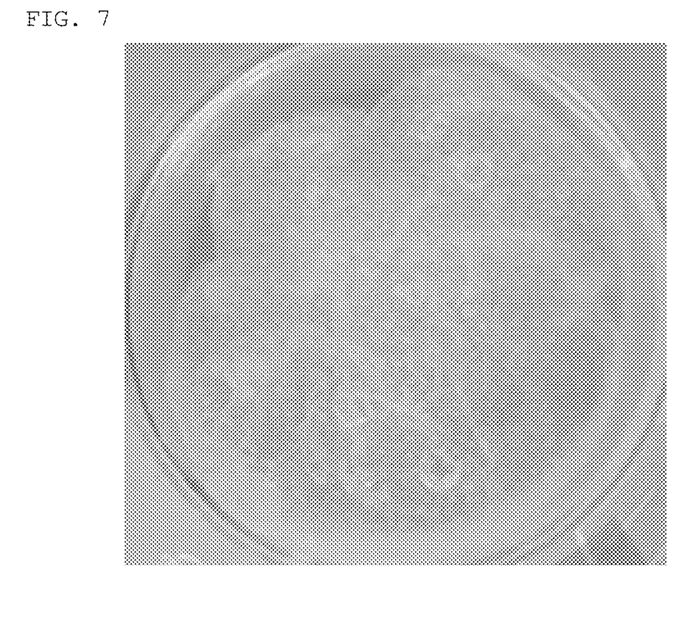
FIG. 7 is a photograph showing the shape of a complex formed by reaction of a mixture of rhamnolipid and sodium alginate with a heavy metal such as copper.
Figure 8:
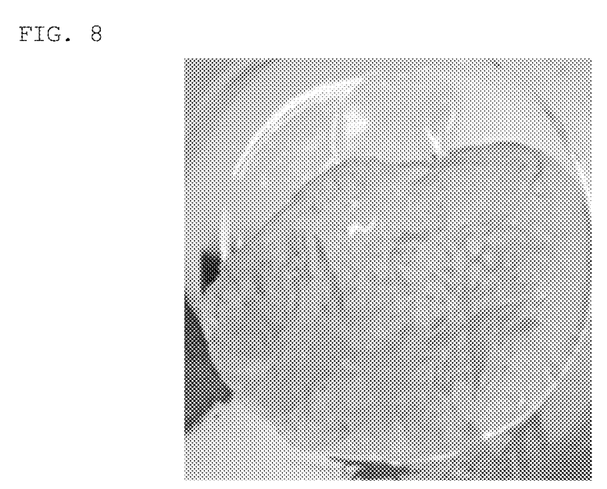
FIG. 8 is a photograph showing the shape of the complex of FIG. 7 after separation from the liquid.

The mixture of rhamnolipid and sodium alginate is capable of forming a complex when reacted with heavy metals such as copper, etc., as shown in FIG. 7. The complex thus formed is in a jelly-like phase and is thus easily separated from the liquid, as shown in FIG. 8.

Specifically, the mixture of rhamnolipid and sodium alginate is formed into a long chain structure, the long chain structure functioning to desorb heavy metals contained in solids, etc. and to leach the same in a liquid phase, and the leached heavy metal or liquid heavy metal is coupled with the long chain structure to form a complex. As the complex formed by the long chain structure is enlarged, the visual recognition efficiency is further increased.

Figure 9:
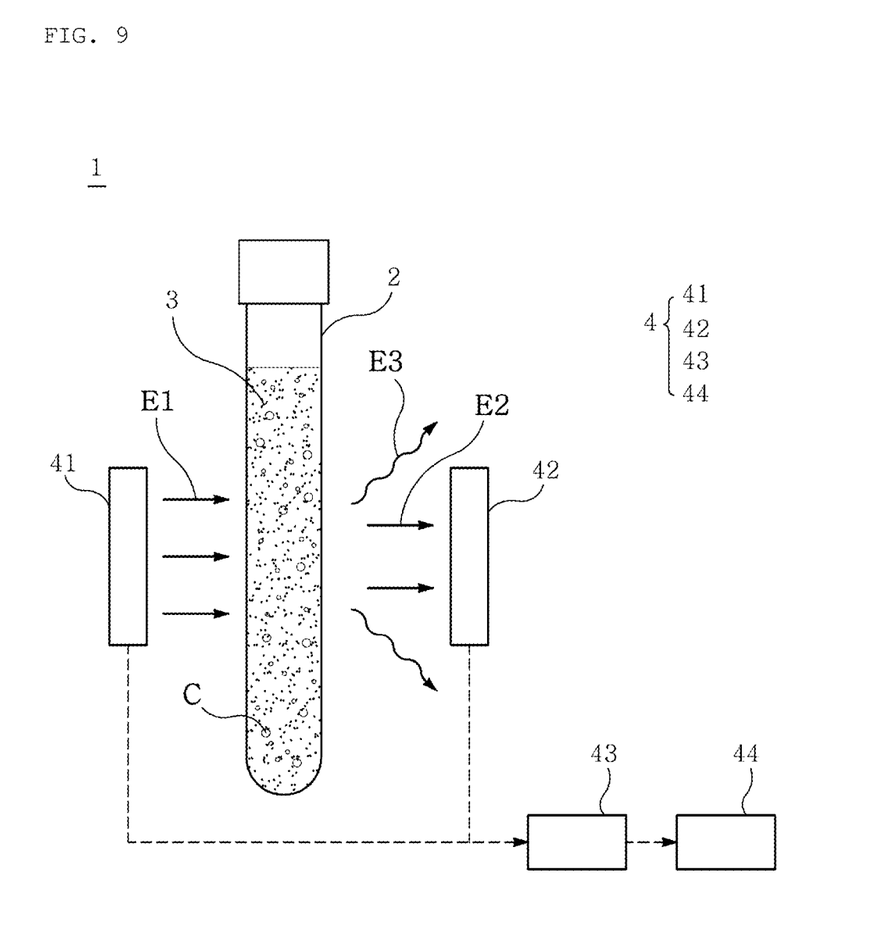
FIG. 9 schematically shows another example of the kit of the present disclosure.

Meanwhile, in the present disclosure, in addition to the experimenter determining whether or not the heavy metal is present in the sample by visually examining the complex, a display part 4 is further included, as shown in FIG. 9, thus providing an embodiment in which the presence or absence of the heavy metal is displayed as data so that the presence or absence of the heavy metal in the sample can be more objectively observed.

In the present embodiment, the kit 1 is configured to further include the display part 4, in addition to the receiving member 2 and the diagnostic solution 3. The display part 4 includes a light irradiation module 41, radiating light to one side of the receiving member 2, a light acquisition module 42, obtaining light transmitted to the opposite side of the receiving member 2, an analysis module 43, comparing the amount of light radiated by the light irradiation module 41 with the amount of light obtained by the light acquisition module 42 to obtain a result value, and a display module 44, displaying the result value of the analysis module 43.

The light irradiation module 41 serves to radiate light to the receiving member 2 by known irradiation means such as an LED, etc.

The light E1 radiated to the receiving member 2 using the light irradiation module 41 is scattered by the complex C formed by the reaction between the diagnostic solution 3 and the heavy metal while passing through the receiving member 2. The light E3 refracted by scattering and the light E2 obtained by the light acquisition module 42 are present. Specifically, when a heavy metal is present in the sample, a complex C is formed in the diagnostic solution 3, and this complex C scatters the light radiated by the light irradiation module 41, thus reducing the amount of light E2 obtained by the light acquisition module 42.

With regard to the light acquisition module 42, there are a variety of known techniques, and thus a detailed description thereof will be omitted.

The analysis module 43 compares the amount of light radiated by the light irradiation module 41 with the amount of light obtained by the light acquisition module 42, and the result value is displayed on the display module 44 when exceeding a reference value. This is to allow the user to recognize that the sample is contaminated with heavy metals not only visually but also through data.

When a sample is not included in the diagnostic solution 3, the amount of light obtained by the light acquisition module 42 after radiating a predetermined amount of light using the light irradiation module 41 is determined as a comparison value. The sample is reacted with the diagnostic solution 3, after which the amount of light obtained by the light acquisition module 42 after radiating the same amount of light using the light irradiation module 41 is compared with the above comparison value. When the light amount difference exceeds the reference value, it is considered that the sample is contaminated with heavy metals, so a certain notification is output on the display module 44. Here, the reference value is a numerical value previously input to the analysis module 43, and may be a light amount difference when heavy metal content in an allowable limit is contained in the sample.

Figure 10:
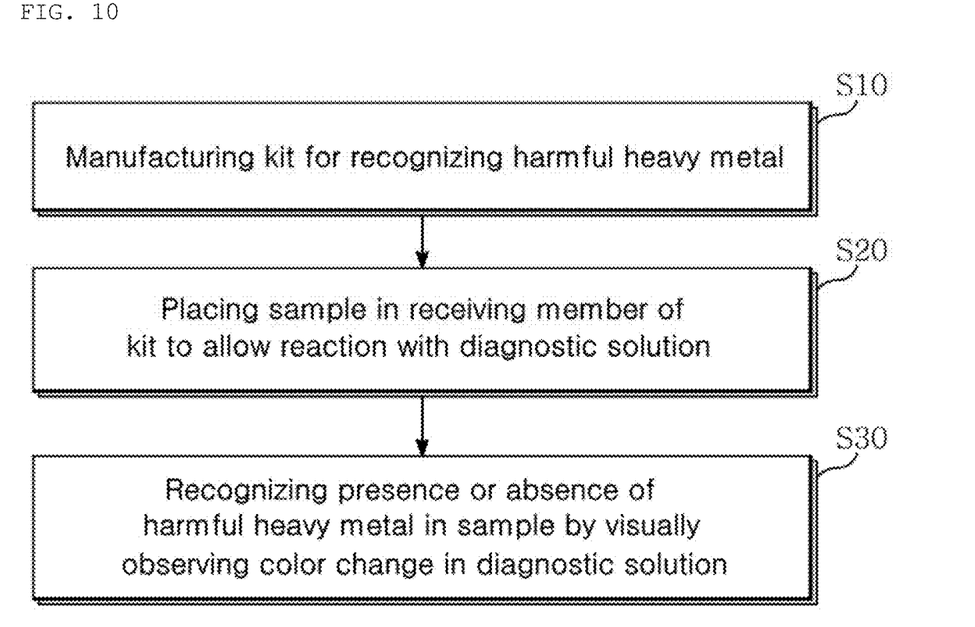
FIG. 10 is a block diagram showing a process of the present disclosure.

As shown in FIG. 10, the method of the present disclosure includes manufacturing the above kit for recognizing a harmful heavy metal (S10), placing a sample in the receiving member of the kit to allow the sample to react with the diagnostic solution (S20), and recognizing the presence or absence of the harmful heavy metal in the sample by visually observing the color change in the diagnostic solution (S30).

In the step of manufacturing the kit for recognizing a harmful heavy metal (S10), the diagnostic solution is prepared by mixing rhamnolipid and sodium alginate solutions at a concentration ratio of 2:1.

Next, in the step of placing the sample in the receiving member of the kit to allow the sample to react with the diagnostic solution (S20), the sample is placed in the receiving member and allowed to react with stirring for 10 to 20 sec, after which the receiving member is allowed to stand for 1 min to 2 min.

Next, in the step of recognizing the presence or absence of the harmful heavy metal in the sample by visually observing the color change in the diagnostic solution (S30), when the heavy metal is present in the sample, a visually recognizable complex is formed in the diagnostic solution, as described above, and the user is capable of determining the presence or absence of the heavy metal in the sample through the complex thus formed.

Moreover, while not illustrated in FIG. 10, in order to further increase the objectivity of judgment, the method of the present disclosure may further include recognizing the presence of absence of the harmful heavy metal in the sample based on data on radiated light using the display part 4 (S40).

In S40, a predetermined amount of light is radiated to one side of the receiving member 2, the light transmitted to the opposite side of the receiving member 2 is obtained, and the amount of light thus obtained is analyzed with a comparison value to thus display the presence or absence of the heavy metal in the sample. This mechanism is the same as described above and a description thereof is thus omitted.

Test Example

In order to exclude interference factors from physical and chemical reactions, deionized water was used to prepare a sodium alginate aqueous solution having a concentration of 2% and a rhamnolipid aqueous solution having a concentration of 1%, respectively, after which these two aqueous solutions were mixed to afford a diagnostic solution.

The diagnostic solution was placed in a test tube (a diameter of 13 mm and a height of 10 cm).

Meanwhile, 3 ml of a harmful heavy metal solution containing copper (Cu) or zinc (Zn), serving as a test target, was placed in the test tube, after which the test tube was covered with a lid and then vigorously stirred for 10 sec so that the reaction occurred, after which the test tube was allowed to stand for 1 min in a test tube holder.

Thereafter, the physical properties of the diagnostic solution in the test tube changed depending on the presence or absence of copper (Cu). It was observed that the pale yellow color of the diagnostic solution in the test tube became faded, that is, became less saturated, in the presence of copper (Cu).

Moreover, it was observed that the color change in the diagnostic solution and the amount of the complex that formed were increased with an increase in the concentration of the copper (Cu) component.

Observation results similar to the above results were also shown in the presence of zinc (Zn) under the same conditions, in addition to copper (Cu).

Based on these observation results, it is possible to determine the presence or absence of harmful heavy metals including copper (Cu) or zinc (Zn) in the liquid (qualitative evaluation) and the degree of contamination with harmful heavy metals (quantitative evaluation).

Here, the color change and the amount of the complex that famed, among the observation results, varied depending on the type of harmful heavy metal component. When using samples such as sediment, soil, deep-sea mining tailings, and the like, as well as harmful heavy metals in the liquid, results similar to the above results could be obtained, thus showing that the present disclosure can be applied to solid samples.

The above observation results can be used as an index for qualitative and quantitative evaluation.

Although the preferred embodiments of the present disclosure have been disclosed for illustrative purposes, those skilled in the art will appreciate that various modifications, additions and substitutions are possible, without departing from the scope and spirit of the invention as disclosed in the accompanying claims.

What is claimed is:

1. A method of identifying the presence of a heavy metal pollutant at a pollution site and outside of a laboratory setting, comprising:
   providing a receiving member containing a diagnostic solution with a biosurfactant consisting of a mixture of sodium alginate and rhamnolipid;
   placing a sample with a heavy metal pollutant in the receiving member and reacting the sample with the diagnostic solution to form a complex between the diagnostic solution and the heavy metal pollutant;
   and qualitatively determining the presence of the heavy metal pollutant in the receiving member by a color change in the diagnostic solution, which is observed visually unassisted outside of the laboratory, and
   quantitatively determining the concentration of the heavy metal pollutant in the receiving member by the amount of the complex consisting of the heavy metal pollutant and the biosurfactant, which is observed visually unassisted outside of the laboratory.

2. The method of claim 1, further comprising qualitatively determining the presence of the heavy metal pollutant in the receiving member by comparing an amount of light transmitted to the receiving member to an amount of light on the opposite side of the receiving member.

3. The method of claim 2, wherein the amount of light is transmitted from a light irradiation module and the amount of light on the opposite side of the receiving member is received by a light acquisition module, a predetermined amount of light is radiated to one side of the receiving member, light transmitted to an opposite side of the receiving member is obtained, and an amount the amounts of light thus obtained is analyzed with a comparison value by an analysis module to display a presence of the heavy metal pollutant in the sample in a display module.

4. The method of claim 1, wherein the complex is formed by an ion exchange reaction of the heavy metal pollutant and the biosurfactant, and is visually recognizable.

5. The method of claim 1, wherein the receiving member is a test tube, and the biosurfactant is the mixture of the sodium alginate and the rhamnolipid is at a concentration ratio of 2 : 1.

6. The method of claim 1, wherein the heavy metal is copper (Cu) or zinc (Zn).

7. The method of claim 4, wherein the amount of the complex formed is in proportion to the amount of the heavy metal pollutant in the sample.

8. The method of claim 4, wherein the color change occurs when the biosurfactant reacts with the heavy metal pollutant in the sample.

9. The method of claim 1, wherein the receiving member and the diagnostic solution are included in a kit.

10. The method of claim 3, wherein the receiving member, the diagnostic solution, the light irradiation module, the light acquisition module, the analysis module and the display module are included in a kit.

11. The method of claim 1, wherein the receiving member is a test tube.

12. The method of claim 1, wherein the biosurfactant includes a plurality of biosurfactant threads.

13. The method of claim 12, the plurality of biosurfactant threads are a combination of at least one sodium alginate molecule and one rhamnolipid molecule.

* * * * *